United States Patent [19]

Carmen et al.

[11] Patent Number: 4,969,882

[45] Date of Patent: Nov. 13, 1990

[54] BAG FOR SEPARATION AND ISOLATION OF BLOOD COMPONENTS

[75] Inventors: Raleigh A. Carmen, Concord; Barry S. Leng, Pleasant Hill; Willie J. Lewis, Oakland; Edward J. Nelson, San Rafael, all of Calif.

[73] Assignee: Miles Laboratories, Inc., Elkhart, Ind.

[21] Appl. No.: 879,745

[22] Filed: Jun. 27, 1986

Related U.S. Application Data

[63] Continuation of Ser. No. 700,793, Feb. 11, 1985, Pat. No. 4,892,537.

[51] Int. Cl.$^5$ .............................................. A61B 19/00
[52] U.S. Cl. .................................................. 604/410
[58] Field of Search ................. 604/5, 6, 407–410, 604/404; 210/516, 740, 744, 789, 929; 494/20, 21

[56] References Cited

U.S. PATENT DOCUMENTS

| | | | |
|---|---|---|---|
| 2,661,741 | 12/1953 | Puckman | 604/408 |
| 2,693,189 | 11/1954 | Ryan | 604/408 |
| 4,224,942 | 9/1980 | Wu et al. | 604/6 |
| 4,278,198 | 7/1981 | Norton et al. | 604/408 |
| 4,322,298 | 3/1982 | Peridsky | 604/6 |
| 4,413,771 | 11/1983 | Rohde et al. | 494/21 |
| 4,413,772 | 11/1983 | Rohde et al. | 494/21 |
| 4,413,773 | 11/1983 | Rohde et al. | 494/21 |
| 4,416,778 | 11/1983 | Rogers | 210/516 |
| 4,582,606 | 4/1986 | McCarty | 210/516 |
| 4,892,537 | 1/1990 | Carmen et al. | 604/408 |

OTHER PUBLICATIONS

Abstract by G. R. Honig et al., "Evaluation of a Simple Procedure for the Preparation of Erythrocyte Concentrates Enriched in Yound Cells for Transfusion", Blood, V.60, M5, Supplement 1, p. 178a, Nov. 1982.

Primary Examiner—C. Fred Rosenbaum
Assistant Examiner—Sharon Rose
Attorney, Agent, or Firm—James A. Giblin

[57] ABSTRACT

A generally flat, elongated edge-sealed polymeric blood bag having a length to width ratio of at least 2 to 1 and one end portion in tapering communication with a connected tubing. When the bag is filled with a mixture of blood components which are then separated, the tapering end portion expands to form a funnel-like guide for directing a separated component from the bag through the tubing in a substantially unobstructed manner. Bag is especially useful for separating and isolating the components of a neocyte/gerocyte red blood cell mixture.

30 Claims, 2 Drawing Sheets

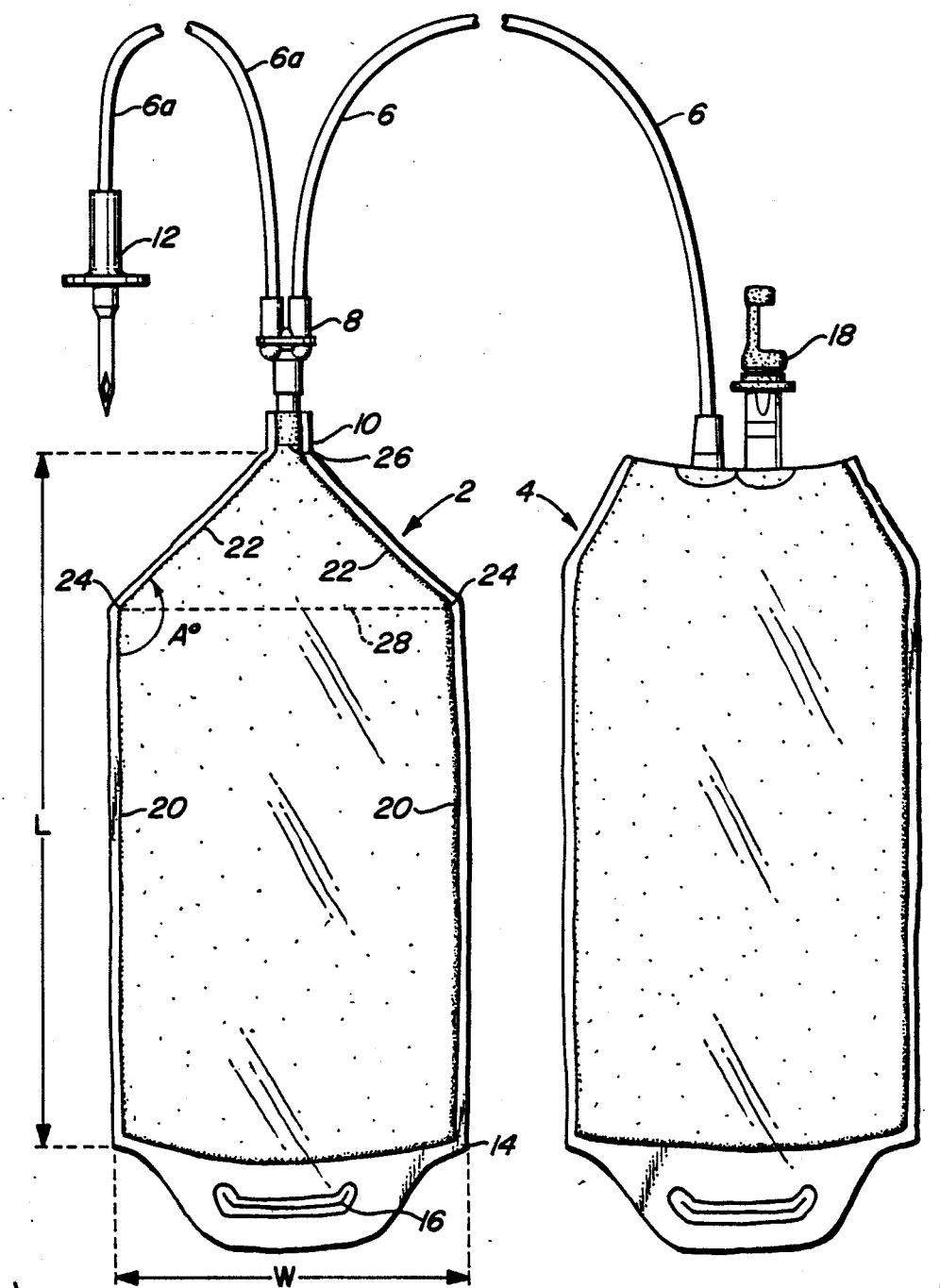
FIG._1.

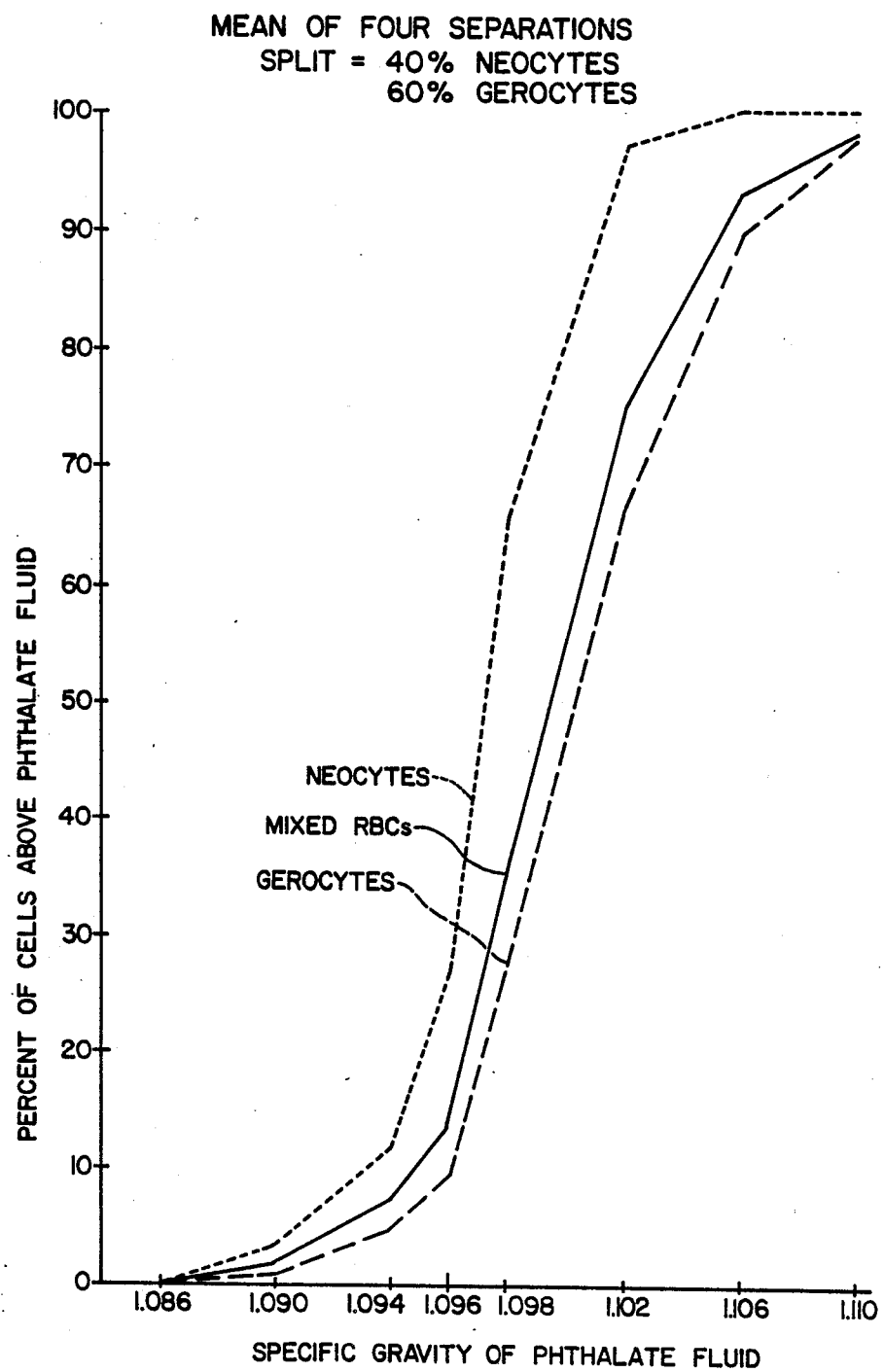
FIG._2.

BAG FOR SEPARATION AND ISOLATION OF BLOOD COMPONENTS

This application is a continuation of application Ser. No. 06/700,793, filed Feb. 11, 1985, now U.S. Pat. No. 4,892,537.

BACKGROUND OF THE INVENTION

1. Field

This disclosure is concerned generally with flexible plastic bags used for collecting, processing and storing of blood and blood components. The disclosure is especially concerned with a blood bag found useful for separating and isolating red cells on the basis of their relative ages using density gradient separation techniques.

2. Prior Art

The manufacture and use of flexible, plastic containers (bags) for the collection, processing and storage of blood and blood components is well known. Whole blood from a donor is typically obtained via venipuncture and collected via tubing in a so-called donor bag. The donor bag may or may not be connected via tubing to one or more so-called satellite or transfer bags. When connected to at least one transfer bag, the donor/transfer bag combination is commonly referred to as a "multiple" blood bag system which may include one, two, or three transfer bags, all in sealed communication with the donor so that, once blood or blood components are introduced into the system, the whole blood or its components may be moved from one bag to another by external manipulation (of valves, etc.), thereby avoiding or minimizing contamination.

In a typical multiple blood bag application, whole blood collected into a donor bag and the connected but empty transfer bag(s) are placed in a centrifuge cup designed to hold the filled donor bag in a generally upright position. The bag contents are then centrifuged to separate whole blood into its lighter serum component and its heavier red blood cell component. By manipulating a valve (usually within the system), the upper plasma may then be expressed into one of the transfer bags, possibly for further processing (e.g. into platelet-rich and platelet-poor components which may be expressed into other connected transfer bags). The separated platelet-poor plasma component may be subsequently fractionated into a variety of other products useful in so-called component therapy (clotting factors, immune serum globulins, albumin, etc.).

In the first separation of plasma from red blood cells in a centrifuged donor bag, the upper plasma portion is often removed from the donor bag using a relatively simple device known as a plasma expressor. The expressor simply squeezes the donor bag, until the plasma is fully expressed out of the bag, typically into a connected transfer bag. At this stage, the separation is fairly approximate and a fine line of demarcation separating the plasma from the packed red cells is generally not critical. In subsequent separations, however, finer separations do become important.

In patent application Ser. No. 585,793 filed in the names of S. Wada et al on Mar. 2, 1984 and entitled, "Container for Fine Separation of Blood and Blood Components", a blood bag for separating white blood cells from platelets is shown. In that disclosure, a conventional blood bag is modified at the bottom to provide a small receptacle for collection and isolation of white blood cells (WBC) from a platelet/WBCs mixture. That disclosure focuses on minimizing the interface between the separated platelets and WBCs by carefully controlling the volume and dimensions of the continuous receptacle and providing a centrifuge insert adapted to accommodate the bag and receptacle.

In U.S. Pat. No. 3,911,918 issued to Turner, there is disclosed an hour-glass shaped plastic blood bag comprising several compartments for the separation and isolation of blood components. That bag is capable (after component separation) of being separated to form a number of individual storage compartments for the separated components. As pointed out in that patent, prior art blood storage containers previously had not been detailed in size and shape to contain a predetermined quantity of blood or a blood component (such as plasma) in separate compartments.

More recently in U.S. Pat. No. 4,416,778 to Rogers, there is disclosed a dual compartment plastic blood bag in which the two compartments are connected via a tubing. The tubing includes a valve adapted to open only after a given centrifugation force is obtained. The bag is said to be especially useful for separating less dense and relatively younger red blood cells (neocytes) from more dense and relatively older red blood cells (gerocytes). As pointed out in that patent, the teachings of which are incorporated herein by reference to it, the use of neocytes is thought to be useful in minimizing iron overload possibilities in patients who depend on repeated blood transfusions.

To date, the primary method used for separating various blood components is simple centrifugation using blood bags (either conventional bags or specially designed bags such as those shown in the above patents) or a specialized mechanical apparatus. One apparatus useful for separating blood components, including neocytes and gerocytes, is an instrument known as an IBM Model 2991 blood cell separator.

Unfortunately, the bags and apparatus available for fine separation of blood components tend to be fairly complex and expensive, thus limiting their use. We have investigated various ways of providing simpler, less costly methods and devices for the separation and isolation of blood components, especially the separation of neocytes and gerocytes. Quite surprisingly, we found that by making relatively inexpensive modifications to conventional blood bags, we can obtain blood component separation and isolation comparable to that obtained using specially designed and complicated bags or specialized and costly machines. Details of our bag are disclosed below.

SUMMARY OF THE INVENTION

Our bag for the separation and isolation of blood components comprises a generally flat, elongated plastic bag which has a length to width ratio of at least 2 to 1 and a top end in tapering communication with a connected tubing. In use, a blood component mixture is introduced into the bag. The mixture is then separated into its desired components using conventional means (e.g. centrifugation according to achieve a pre-determined density gradient). After separation, the weight of the components to be separated is determined, and the upper component is expressed out of the tapered top of the bag which, when expanded by the bag's contents, forms a funnel-like guide for directing the separated component from the bag and through the tubing in a substantially unobstructed manner. In very preferred embodiments, the elongated bag has a length to width ratio of at least 2.5 to 1 and has a pair substantially parallel major sides (edges) continuous with converging minor sides (edges) defining an obtuse angle of at least about 110°, preferably about 145°. A preferred bag has a volume of about 275 ml and is pre-connected via a single tubing to another bag to form a "double" useful, in combination, for the separation and isolation of neocytes from a mixture of neocytes and gerocytes.

BRIEF DESCRIPTION OF THE FIGURES

FIG. 1 is a plan view illustrating the blood bag of this disclosure pre-connected via tubing to another bag.

FIG. 2 is a graph showing the neocyte/gerocyte separations obtained using the bag of this disclosure.

SPECIFIC EMBODIMENTS

Unlike, the generally square (5"×6"), flat conventional blood bags having at least two ports positioned along the top edge of the bag, our bag comprises a substantially elongated bag (length at least twice width) having no top edge and only a single port positioned at the end of converging top sides. Our bag is illustrated in FIG. 1 where the bag 2 is shown connected in sealed communication via conventional polyvinyl chloride (PVC) tubing 6 to a second bag 4. Bags 2 and 4 may be made from conventional plastic films known to those skilled in the art such as those shown in U.S. Pat. No. 4,280,497 and U.S. Pat. No. 4,222,379. The bags 2 and 4 are generally flat and formed by conventional means such as simple edge sealing at edges 14. Bags 2 and 4 may also include conventional end flaps having orifices 16 for hanging the bags in an inverted position.

As can be seen by looking at bag 2 (the bag of this invention), it is considerably elongated having length (L) to width (W) dimensions of at least 2 to 1. In addition, it includes substantially parallel major sides (edges) 20 comprising most of the bag length (at least 50%) which are continuous with converging minor sides 22 which meet at point 24 forming an obtuse angle A which is at least 110°, preferably about 145°. Converging edges are designed to guide the filled bag contents in a substantially unobstructed manner (in funnel-like fashion) to exit port 26 which is continuous with neck portion 10 sealed about exit port 26.

Exit port 26 communicates with a conventional plastic 2-for-1 "Y" piece 8 which in turn communicates with tubing 6 connected to bag 4 (which includes sealed exit port 18) and tubing 6a which communicates with a conventional spike 12 through which the initial mixture is introduced into bag 2. Since the "double" bag of FIG. 1 is ideally suited for separating the components of a neocyte/gerocyte mixture (see below), the spike 12 connected to tubing 6a is adapted to be inserted into one of the exit port of a conventional donor bag containing mixed red blood cells after the plasma has been expressed.

Bag 4 is preferably also flat and about the same size as bag 2 so that when bag 2 is filled with mixed cells (assuming a somewhat cylindrical shape due to expansion), empty and flat bag 4 may be wrapped around filled bag 2 for insertion into a centrifuge cup adapted to receive both in that manner. In one embodiment, a conventional valve may be associated with tubing 6 (either externally as, for example, a clamp or internally as, for example, a pierceable membrane or frangible in-line pierceable or frangible valve). Such valve may close communication to bag 4 until the separated contents of the bag 2 (upper contents after centrifugation) are ready for transfer to bag 4.

As example of how the bag may be used to separate neocytes from gerocytes using the 275 ml bag of FIG. 1 follows: First, about 275 ml of red blood cells of mixed age are drawn into bag 2 via tubing 6a using spike 12. Empty bag 4 is wrapped about the filled bag 2 and both are inserted into a special centrifuge cup insert about 63 mm in diameter and about 130 mm deep and generally conforming to the volume of the filled bag. Centrifugation proceeds at 4000 xg for 30 minutes or until optimal separation is achieved. The bag(s) are then removed and the upper neocyte component is expressed from the bag 2 into bag 4 as follows: The weight of the upper component is calculated using the hematocrit, the desired neocyte/gerocyte fraction, and the total weight of pre-separated red cells (the original unseparated RBC mixture). The upper component is expressed using a conventional plasma expressor from bag 2 into bag 4 until the desired weight is transferred. Tube 6 is sealed and bag 4 containing the neocyte fraction is removed.

SEPARATION STUDIES

The above separation of neocytes from a mixed neocyte/gerocyte RBC populations is illustrated in FIG. 2. FIG. 2 is a graph which shows density distribution curves of neocytes (dotted line), gerocytes (dashed line), and pre-separation red cells (solid line).

Using the method of Danon and Marikovsky, J. Lab. & Clin. Med., p. 668–674, October, 1964, the density distributions of cells from the least dense (youngest) to the most dense (oldest) were determined for a sample of red blood cells, using phthalate esters as separating liquids. Theoretically a perfect neocyte separation would have 100% of its cells below the mean (50%) specific gravity of the pre-separation cells.

The mean density of the pre-separation cells on the graph of FIG. 2 is 1.0995. Half of the cells are above the phthalate fluid of that density and half are below. At the same specific gravity (1.0995) on the neocyte curve 77.5% of the cells in the neocyte fraction are lighter than the mean specific gravity of the pre-separation RBC sample. As shown by the graph of FIG. 2, the mean specific gravity of the pre-separation sample is about 1.0995; the mean specific gravity of the neocyte portion is about 1.0972; and the mean specific gravity of the gerocyte portion is about 1.1003.

These data show that a satisfactory separation of younger (less dense) and older (more dense) cells is achieved with this blood bag system. Our separation compared favorably with two other techniques (using a mechanical cell separator and a multi-chambered bag).

It should be understood that the above example should be considered merely illustrative of the invention disclosed herein and that, given this disclosure, variations will occur to those skilled in the art. Accordingly, it is intended that the invention disclosed herein should be limited only by the following claims.

We claim:

1. A method of separating neocytes from gerocytes in a mixture of red blood cells comprising neocytes and gerocytes, the method comprising the steps of
   (1) introducing the mixture into an elongated polymeric bag having a length to width ratio of at least 2 to 1 and an upper end portion which is in tapering communication with an exit port and determining the total weight of the mixture;

(2) centrifuging the mixture under conditions sufficient to separate the mixture components into a lower more dense gerocyte fraction and an upper less dense neocyte fraction; and (3) expressing the upper neocyte fraction through the exit port under conditions sufficient to assure the transfer of a determined weight of the neocyte fraction from the bag.

2. The method of claim 1 wherein the upper portion of the bag forms a funnel-like guide for directing the expressed upper neocyte fraction from the bag and through the exit port in a substantially unobstructed manner.

3. The method of claim 1 wherein the length to width ratio is at least about 2.5 to 1.

4. The method of claim 1 wherein the bag is generally flat having sides defined by major, substantially parallel edges continuous with minor, converging edges and defining an obtuse angle of at least about 110°.

5. The method of claim 4 wherein the angle is about 145°.

6. The method of claim 6 wherein exit port is continuous with a plastic tubing and in communication with at least one other polymeric bag.

7. The method of claim 1 wherein the centrifugation is under conditions sufficient to achieve a pre-determined red blood cell density gradient.

8. The method of claim 1 wherein the weight of the neocytes to be separated is determined prior to expression out of the bag.

9. The method of claim 1 wherein the bag has a volume of about 275 ml.

10. The method of claim 1 wherein the bag is pre-connected via the tubing to another bag and the tubing includes valve means between the bags.

11. In a method of separating neocytes from red blood cells comprising a mixture of neocytes and gerocytes, the method comprising centrifuging a blood bag containing the mixture under conditions sufficient to assure the gradient density separation of the less dense neocytes from the more dense gerocytes and then separating the neocytes, the improvements which comprise using an elongated bag having a length to width ratio of at least 2 to 1 to contain the mixture, determining the total weight of the mixture and expressing a determined weight of neocytes from the bag after centrifugation.

12. The method of claim 11 wherein the bag comprises an upper end portion which is in tapering communication with an exit port.

13. The method of claim 11 wherein the upper end portion forms a funnel-like guide for directing the neocytes from the bag in a substantially unobstructed manner.

14. The method of claim 11 wherein the length to width ratio is at least about 2.5 to 1.

15. The method of claim 11 wherein the bag is generally flat having sides defined by major, substantially parallel edges continuous with minor, converging edges and defining an obtuse angle of at least about 110°.

16. The method of claim 15 wherein the angle is about 145°.

17. The method of claim 11 wherein the bag is connected via tubing to another bag.

18. The method of claim 11 wherein the bag has a volume of about 275 ml.

19. The method of claim 11 wherein the centrifugation is under conditions sufficient to achieve a pre-determined density gradient and the weight of the neocytes to be separated is determined prior to separating the neocytes from the bag.

20. A method of separating less dense neocytes from more dense gerocytes in a red blood cell mixture comprising neocytes and gerocytes, the method comprising the steps of (1) introducing the mixture into the first blood bag of a blood bag system comprising a first bag connected via tubing to a second bag, the system including a valve means closing communication between the two bags and determining the weight of the mixture;

(2) centrifuging the contents of the first bag under conditions sufficient to separate the less dense neocytes from the more dense gerocytes;

(3) opening the valve means between the bags; and (4) expressing a determined weight of neocytes from the first bag into the second bag.

21. The method of claim 20 wherein the first bag has an upper tapered portion in communication with an exit-port connected to the tubing, the tapered portion adapted to expand when the first bag contains the red blood cells and adapted to form a funnel-like guide for directing neocytes from the first bag in a substantially unobstructed manner after the centrifugation step.

22. The method of claim 20 wherein the length to width ratio of the first bag is at least about 2 to 1.

23. The method of claim 22 wherein the length to width ratio is at least about 2.5 1.

24. The method of claim 20 wherein the first bag is generally flat, having sides defined by major substantially parallel edges continuous with minor converging edges and defining an obtuse angle of at least about 110°.

25. The method of claim 24 wherein the angle is about 145°.

26. The method of claim 20 wherein the first bag has a volume of about 275 ml.

27. The method of claim 20 wherein the weight of the neocytes to be separated is determined prior to separating the neocytes from the first bag.

28. The method of claim 20 wherein the centrifugation is under conditions sufficient to achieve a pre-determined density gradient of the red blood cell mixture.

29. The method of claim 20 wherein the valve between the two bags is a clamp.

30. The method of claim 20 wherein the valve is a frangible valve.

* * * * *